(12) United States Patent
Colla et al.

(10) Patent No.: US 6,363,270 B1
(45) Date of Patent: Mar. 26, 2002

(54) MONITORING THE OCCURRENCE OF APNEIC AND HYPOPNEIC AROUSALS

(75) Inventors: Gregory Alan Colla, North Sydney; John William Ernest Brydon, Waverton, both of (AU)

(73) Assignee: ResMed Limited, North Ryde (AU)

( * ) Notice: Subject to any disclaimer, the term of this patent is extended or adjusted under 35 U.S.C. 154(b) by 0 days.

(21) Appl. No.: 09/465,048

(22) Filed: Dec. 16, 1999

Related U.S. Application Data

(63) Continuation of application No. 08/894,093, filed on Dec. 22, 1997.

(30) Foreign Application Priority Data

Apr. 11, 1995 (AU) .................................................. PN2365

(51) Int. Cl.[7] .................................................. A61B 5/00
(52) U.S. Cl. .................... 600/324; 600/484; 600/547
(58) Field of Search ........................... 600/306, 324, 600/483, 484, 529, 547

(56) References Cited

U.S. PATENT DOCUMENTS

| | | |
|---|---|---|
| 2,904,033 A | 9/1959 | Shane |
| 3,099,985 A | 8/1963 | Wilson et al. |
| 3,502,100 A | 3/1970 | Jonson |
| 3,559,638 A | 2/1971 | Potter |
| 3,595,228 A | 7/1971 | Simon et al. |
| 3,611,801 A | 10/1971 | Paine et al. |
| 3,741,208 A | 6/1973 | Jonsson et al. |
| 3,783,893 A | 1/1974 | Davidson |
| 3,802,417 A | 4/1974 | Lang |
| 3,817,246 A | 6/1974 | Weigl |
| 3,882,847 A | 5/1975 | Jacobs |
| 3,903,875 A | 9/1975 | Hughes |
| 3,914,994 A | 10/1975 | Banner |
| 3,932,054 A | 1/1976 | McKelvey |
| 3,985,467 A | 10/1976 | Lefferson |
| 3,989,037 A | 11/1976 | Franetzki |
| 3,992,598 A | 11/1976 | Welsh et al. |

(List continued on next page.)

FOREIGN PATENT DOCUMENTS

| | | |
|---|---|---|
| AU | 78018/91 | 8/1990 |
| AU | 59270/90 | 12/1990 |
| AU | 62221/90 | 3/1991 |
| AU | 99877/93 | 4/1993 |
| AU | 38608/93 | 7/1993 |

(List continued on next page.)

OTHER PUBLICATIONS

Derwent: Flowmeter for fluids–has turbine transducer and volumetric sensor for simultaneous calibration.

Mark Kantrowitz, Erik Horskotte and Cliff Joslyn; "Answers to Frequently Asked Questions about Fuzzy Logic and Fuzzy Expert Systems" Version 1.24 last modified Feb. 20, 1990.

New: Breas PV 100 CPAP First Class Quality and Function. At the Right Price; Jul. 4, 1998, pp. 1–3.

Prodigy Medical Supplies Co. Ltd.; CPAP.

(List continued on next page.)

*Primary Examiner*—Eric F. Winakur
(74) *Attorney, Agent, or Firm*—Pillsbury Winthrop LLP

(57) ABSTRACT

The occurrence of an arousal in a patient associated with an apneic or hypopneic episode car be determined. Sensors are placed on a patient to obtain signals representative of at least two physiological variables, for example skin conductance, heart rate and blood oxygen concentration. The signals are conditioned by conditioning circuitry, then processed by a processor to correlate at least two thereof. A coincident change in at least two of the processed signals is indicative of the occurrence of an arousal, that in turn indicates an apneic or hypopneic episode has occurred. A patient thus can be diagnosed as suffering conditions such as obstructive sleep apnea.

14 Claims, 5 Drawing Sheets

U.S. PATENT DOCUMENTS

| | | |
|---|---|---|
| 3,995,661 A | 12/1976 | Van Fossen |
| 4,006,634 A | 2/1977 | Billette et al. |
| 4,083,245 A | 4/1978 | Osburn |
| 4,109,749 A | 8/1978 | Sweet |
| 4,119,096 A | 10/1978 | Drews |
| 4,206,754 A | 6/1980 | Cox et al. |
| 4,249,527 A | 2/1981 | Ko et al. |
| 4,301,833 A | 11/1981 | Donald, III |
| 4,312,235 A | 1/1982 | Daigle |
| 4,320,766 A | 3/1982 | Alihanka et al. |
| 4,322,594 A | 3/1982 | Brisson |
| 4,387,722 A | 6/1983 | Kearns |
| 4,396,034 A | 8/1983 | Cherniak |
| 4,414,982 A | 11/1983 | Durkan |
| 4,433,883 A | 2/1984 | Hochstein |
| 4,448,058 A | 5/1984 | Jaffe et al. |
| 4,449,525 A | 5/1984 | White et al. |
| 4,481,944 A | 11/1984 | Bunnell |
| 4,499,914 A | 2/1985 | Scheblar |
| 4,506,666 A | 3/1985 | Durkan |
| 4,550,615 A | 11/1985 | Grant |
| 4,550,726 A | 11/1985 | McEwen |
| 4,558,710 A | 12/1985 | Eichler |
| 4,570,831 A | 2/1986 | Durkan |
| 4,576,179 A | 3/1986 | Manus et al. |
| 4,579,114 A | 4/1986 | Gray et al. |
| 4,592,880 A | 6/1986 | Murakami |
| 4,595,016 A | 6/1986 | Fertig et al. |
| 4,602,644 A | 7/1986 | DiBenedetto et al. |
| RE32,295 E | 11/1986 | Estes et al. |
| 4,630,514 A | 12/1986 | Atlas |
| 4,648,396 A | 3/1987 | Raemer |
| 4,648,407 A | 3/1987 | Sackner |
| 4,655,213 A | 4/1987 | Rapoport et al. |
| 4,677,975 A | 7/1987 | Edgar et al. |
| 4,680,575 A | 7/1987 | Birnbaum et al. |
| 4,686,974 A | 8/1987 | Sato et al. |
| 4,686,999 A | 8/1987 | Snyder et al. |
| 4,738,266 A | 4/1988 | Thatcher |
| 4,747,403 A | 5/1988 | Gluck et al. |
| 4,773,411 A | 9/1988 | Downs |
| 4,777,963 A | 10/1988 | McKenna |
| 4,795,314 A | 1/1989 | Prybella et al. |
| 4,801,788 A | 1/1989 | Douglass |
| 4,802,485 A | 2/1989 | Bowers et al. |
| 4,802,489 A | 2/1989 | Bowers et al. |
| 4,803,471 A | 2/1989 | Rowland |
| 4,819,629 A | 4/1989 | Jonson |
| 4,823,788 A | 4/1989 | Smith et al. |
| 4,825,802 A | 5/1989 | Le Bec |
| 4,827,922 A | 5/1989 | Champain et al. |
| 4,838,258 A | 6/1989 | Dryden et al. |
| 4,844,085 A | 7/1989 | Gattinoni |
| 4,856,506 A | 8/1989 | Jinotti |
| 4,860,766 A | 8/1989 | Sackner |
| 4,870,960 A | 10/1989 | Hradek |
| 4,870,963 A | 10/1989 | Carter |
| 4,877,607 A | 10/1989 | Beatty |
| 4,913,401 A | 4/1990 | Handke |
| 4,915,103 A | 4/1990 | Visveshwara et al. |
| 4,928,684 A | 5/1990 | Breitenfelder et al. |
| 4,938,210 A | 7/1990 | Shene |
| 4,938,212 A | 7/1990 | Snook et al. |
| 4,944,310 A | 7/1990 | Sullivan |
| 4,957,107 A | 9/1990 | Sipin |
| 4,960,118 A | 10/1990 | Pennock |
| 4,971,065 A | 11/1990 | Pearce |
| 4,972,842 A | 11/1990 | Korten et al. |
| 4,982,738 A | 1/1991 | Griebel |
| 4,989,269 A | 2/1991 | Hakkinen |
| 4,989,599 A | 2/1991 | Carter |
| 5,024,219 A | 6/1991 | Dietz |
| 5,048,515 A | 9/1991 | Sanso |
| 5,052,400 A | 10/1991 | Dietz |
| 5,063,922 A | 11/1991 | Hakkinen |
| 5,065,756 A | 11/1991 | Rapoport |
| 5,069,222 A | 12/1991 | McDonald, Jr. |
| 5,090,248 A | 2/1992 | Cimmino et al. |
| 5,099,635 A | 3/1992 | Scarberry |
| 5,099,837 A | 3/1992 | Russel, Sr. et al. |
| 5,105,354 A * | 4/1992 | Nishimura .................. 600/484 |
| 5,107,830 A | 4/1992 | Younes |
| 5,107,831 A | 4/1992 | Halpern et al. |
| 5,117,819 A | 6/1992 | Servidio et al. |
| 5,129,390 A | 7/1992 | Chopin et al. |
| 5,134,995 A | 8/1992 | Gruenke et al. |
| 5,148,802 A | 9/1992 | Sanders et al. |
| 5,161,541 A | 11/1992 | Bowman et al. |
| 5,165,398 A | 11/1992 | Bird |
| 5,170,798 A | 12/1992 | Riker |
| 5,174,287 A | 12/1992 | Kallok et al. |
| 5,178,138 A | 1/1993 | Walstrom et al. |
| 5,181,525 A | 1/1993 | Kimm et al. |
| 5,183,983 A | 2/1993 | Knop |
| 5,190,048 A | 3/1993 | Wilkinson |
| 5,195,528 A | 3/1993 | Hok |
| 5,199,424 A | 4/1993 | Sullivan et al. |
| 5,203,343 A | 4/1993 | Axe et al. |
| 5,230,330 A | 7/1993 | Price |
| 5,231,979 A | 8/1993 | Rose et al. |
| 5,231,983 A | 8/1993 | Matson et al. |
| 5,233,983 A | 8/1993 | Markowitz |
| 5,239,994 A | 8/1993 | Atkins |
| 5,239,995 A | 8/1993 | Estes et al. |
| 5,245,995 A | 9/1993 | Sullivan et al. |
| 5,259,373 A | 11/1993 | Gruenke et al. |
| 5,271,391 A | 12/1993 | Graves |
| 5,280,784 A | 1/1994 | Kohler |
| 5,293,864 A | 3/1994 | McFadden |
| 5,295,491 A | 3/1994 | Gevins |
| 5,303,698 A | 4/1994 | Tobia et al. |
| 5,303,700 A | 4/1994 | Weismann et al. |
| 5,305,787 A | 4/1994 | Thygesen |
| 5,311,875 A | 5/1994 | Stasz |
| 5,313,937 A | 5/1994 | Zdrojkowski |
| 5,322,057 A | 6/1994 | Raabe et al. |
| 5,335,654 A | 8/1994 | Rapoport |
| 5,335,656 A | 8/1994 | Bowe et al. |
| 5,343,878 A | 9/1994 | Scarberry et al. |
| 5,353,788 A | 10/1994 | Miles |
| 5,360,008 A | 11/1994 | Campbell, Jr. |
| 5,373,842 A | 12/1994 | Olsson |
| 5,388,571 A | 2/1995 | Roberts et al. |
| 5,394,002 A | 2/1995 | Mawhinney |
| 5,398,673 A | 3/1995 | Lambert |
| 5,400,777 A | 3/1995 | Olsson et al. |
| 5,404,871 A | 4/1995 | Goodman et al. |
| 5,413,111 A | 5/1995 | Wilkinson |
| 5,433,193 A | 7/1995 | Sanders et al. |
| 5,438,980 A | 8/1995 | Philips |
| 5,443,061 A | 8/1995 | Champain et al. |
| 5,443,075 A | 8/1995 | Holscher |
| 5,448,996 A | 9/1995 | Bellin et al. |
| 5,458,137 A | 10/1995 | Axe et al. |
| 5,479,920 A | 1/1996 | Piper et al. |
| 5,479,939 A | 1/1996 | Ogino |
| 5,483,969 A | 1/1996 | Testerman et al. |
| 5,490,502 A | 2/1996 | Rapoport et al. |
| 5,492,113 A | 2/1996 | Estes et al. |

| | | | | | | |
|---|---|---|---|---|---|---|
| 5,503,146 | A | 4/1996 | Froehlich et al. | DE | 19536632 A1 | 3/1997 |
| 5,507,282 | A | 4/1996 | Younes | EP | 062 166 A2 | 10/1982 |
| 5,509,404 | A | 4/1996 | Lloyd et al. | EP | 066 451 A1 | 12/1982 |
| 5,513,631 | A | 5/1996 | McWilliams | EP | 0 088 761 | 9/1983 |
| 5,517,983 | A | 5/1996 | Deighan et al. | EP | 0164500 A2 | 3/1985 |
| 5,526,805 | A | 6/1996 | Lutz et al. | EP | 0185 980 | 7/1986 |
| 5,535,738 | A | 7/1996 | Estes et al. | EP | 0236 850 A2 | 9/1987 |
| 5,535,739 | A | 7/1996 | Rapoport et al. | EP | 0872643 A2 | 7/1988 |
| 5,537,997 | A | 7/1996 | Mechlenburg et al. | EP | 298 367 A2 | 1/1989 |
| 5,540,219 | A | 7/1996 | Mechlenburg et al. | EP | 0425092 A1 | 9/1989 |
| 5,540,220 | A | 7/1996 | Gropper | EP | 0452001 A2 | 3/1990 |
| 5,540,733 | A | 7/1996 | Testerman et al. | EP | 038 525 A1 | 9/1990 |
| 5,546,933 | A | 8/1996 | Rapoport et al. | EP | 045092 A1 | 8/1991 |
| 5,546,952 | A | 8/1996 | Erickson | EP | 0481281 A1 | 12/1991 |
| 5,549,106 | A | 8/1996 | Gruenke et al. | EP | 0481 459 A1 | 4/1992 |
| 5,549,655 | A | 8/1996 | Erickson | EP | 481 459 A1 | 4/1992 |
| 5,551,418 | A | 9/1996 | Estes et al. | EP | 0514744 A1 | 11/1992 |
| 5,551,419 | A | 9/1996 | Froehlich et al. | EP | 0540209 A2 | 6/1993 |
| 5,558,099 | A | 9/1996 | Bowman et al. | EP | 606687 A2 | 7/1994 |
| RE35,339 | E | 10/1996 | Rapoport | EP | 0705616 A1 | 9/1994 |
| 5,567,127 | A | 10/1996 | Wentz | EP | 0714 670 A2 | 12/1994 |
| 5,570,682 | A | 11/1996 | Johnson | EP | 0851971 A1 | 5/1995 |
| 5,588,439 | A | 12/1996 | Hollub | EP | 0668210 A2 | 6/1995 |
| 5,598,838 | A | 2/1997 | Servido et al. | EP | 0661071 A1 | 7/1995 |
| 5,605,191 | A | 2/1997 | Lynn | EP | 0171321 A1 | 2/1996 |
| 5,608,647 | A | 3/1997 | Rubsamen et al. | EP | 178 925 A2 | 4/1996 |
| 5,617,846 | A | 4/1997 | Graetz et al. | EP | 0709107 A1 | 6/1996 |
| 5,630,411 | A | 5/1997 | Holscher | EP | 0714670 A2 | 6/1996 |
| 5,632,269 | A | 5/1997 | Zdrojkowski | EP | 0765631 A2 | 4/1997 |
| 5,633,552 | A | 5/1997 | Lee et al. | EP | 0788805 A2 | 8/1997 |
| 5,642,730 | A | 7/1997 | Baran | EP | 0839645 A1 | 5/1998 |
| 5,645,053 | A | 7/1997 | Remmers et al. | FR | 2574 657 A1 | 6/1986 |
| 5,647,351 | A | 7/1997 | Wesimann et al. | FR | 2672 221 A1 | 8/1992 |
| 6,546,054 | | 7/1997 | Cotner et al. | FR | 2682042 A1 | 4/1993 |
| 5,655,520 | A | 8/1997 | Howe et al. | GB | 1432572 | 4/1976 |
| 5,655,522 | A | 8/1997 | Mechlenburg et al. | GB | 1 444053 | 7/1976 |
| 5,660,171 | A | 8/1997 | Kimm et al. | GB | 2 077 444 A | 12/1981 |
| 5,666,946 | A | 9/1997 | Lagenback | GB | 2147506 A | 6/1985 |
| 5,682,878 | A | 11/1997 | Ogden | GB | 2104569 A | 3/1986 |
| 5,685,296 | A | 11/1997 | Zdrojkowski et al. | GB | 2198871 A | 5/1986 |
| 5,701,883 | A | 12/1997 | Hete et al. | GB | 2205 167 A | 11/1988 |
| 5,704,345 | A | 1/1998 | Berthon-Jones | GB | 2 254 700 A | 10/1992 |
| 5,715,812 | A | 2/1998 | Deighan et al. | GB | 2261290 A | 5/1993 |
| 5,730,121 | A | 3/1998 | Hawkins | GB | 2 271 811 A | 4/1994 |
| 5,740,795 | A | 4/1998 | Dryden | GB | 2294400 A | 8/1998 |
| 5,794,615 | A | 8/1998 | Estes | JP | 54-104369 | 8/1979 |
| 5,797,852 | A | 8/1998 | Karakasoglu et al. | JP | 60-212607 | 10/1985 |
| 5,803,066 | A | 9/1998 | Rapoport et al. | JP | 62-103297 | 4/1987 |
| 5,823,187 | A | 10/1998 | Estes et al. | JP | 63-275362 | 11/1988 |
| 5,845,636 | A | 12/1998 | Gruenke et al. | JP | 2-173397 | 12/1988 |
| 5,922,382 | A | 7/1999 | Sullivan et al. | JP | 70516 A | 3/1992 |
| 5,927,829 | A | 7/1999 | Harris et al. | JP | 4-70516 | 3/1992 |
| 6,091,973 | A * | 7/2000 | Colla et al. ................. 600/324 | JP | 6-249742 A | 8/1994 |
| | | | | JP | 06249741 A | 9/1994 |
| | FOREIGN PATENT DOCUMENTS | | | JP | 07280009 | 10/1995 |
| | | | | JP | 8019010 A | 1/1996 |
| AU | 48748/93 | 9/1993 | | SE | 1710064 A1 | 2/1992 |
| AU | 52628/93 | 7/1994 | | SE | 467041 B | 5/1992 |
| AU | 79174/94 | 6/1995 | | WO | WO 80/01044 | 5/1980 |
| AU | 34471/95 | 2/1996 | | WO | WO 82/03326 | 10/1982 |
| AU | 4071195 | 4/1996 | | WO | WO 82/03548 | 10/1982 |
| AU | 34354/95 | 5/1996 | | WO | WO 86/05986 | 10/1986 |
| AU | 39190/95 | 6/1996 | | WO | WO 86/06969 | 12/1986 |
| AU | 42027/97 | 2/1998 | | WO | WO 87/02577 | 5/1987 |
| DE | 459104 | 4/1928 | | WO | WO 88/10108 | 12/1988 |
| DE | 3015279 | 10/1981 | | WO | WO 90/14121 | 11/1990 |
| DE | 884567 A1 | 6/1984 | | WO | WO 91/12051 | 8/1991 |
| DE | 3402603 A1 | 8/1985 | | WO | WO 91/19456 | 12/1991 |
| DE | 3537507 A1 | 4/1987 | | WO | WO 92/11064 | 7/1992 |
| DE | 3539073 A1 | 5/1987 | | WO | WO 92/15353 | 9/1992 |
| DE | 4432219 C1 | 4/1996 | | WO | WO 89/09665 | 10/1992 |
| DE | 29612119 B1 | 12/1996 | | | | |

| | | |
|---|---|---|
| WO | WO 92/22244 | 12/1992 |
| WO | WO 93/08857 | 5/1993 |
| WO | WO 93/09834 | 5/1993 |
| WO | WO 93/0887 | 6/1993 |
| WO | WO 93/21982 | 11/1993 |
| WO | WO 93/24169 | 12/1993 |
| WO | WO 94/04071 | 3/1994 |
| WO | WO 94/16759 | 8/1994 |
| WO | WO 94/20018 | 8/1994 |
| WO | WO 94/20051 | 9/1994 |
| WO | WO 94/23780 | 10/1994 |
| WO | WO 95/32016 | 11/1995 |
| WO | WO 95/34917 | 12/1995 |
| WO | 96/16688 | 6/1996 |
| WO | WO 96/32055 | 10/1996 |
| WO | WO 96/36279 | 11/1996 |
| WO | WO 96/40337 | 12/1996 |
| WO | WO 96/41571 | 12/1996 |
| WO | WO 97/02064 | 1/1997 |
| WO | WO 97/05824 | 2/1997 |
| WO | WO 97/10868 | 2/1997 |
| WO | WO 97/10019 | 3/1997 |
| WO | WO 97/14354 | 4/1997 |
| WO | WO 97/10752 | 5/1997 |
| WO | WO 97/15343 | 5/1997 |
| WO | WO 97/20499 | 6/1997 |
| WO | WO 97/22377 | 6/1997 |
| WO | WO 97/28838 | 8/1997 |
| WO | WO 97/41812 | 11/1997 |
| WO | WO 98/06449 | 2/1998 |
| WO | WO 98/25662 | 8/1998 |
| WO | WO 98/33433 | 8/1998 |
| WO | WO 98/35715 | 8/1998 |
| WO | WO 98/36338 | 8/1998 |
| WO | WO 98/36545 | 8/1998 |
| WO | WO 98/47554 | 10/1998 |
| WO | WO 98/52467 | 11/1998 |
| WO | WO 98/57691 | 12/1998 |

OTHER PUBLICATIONS

Puritan Bennett; Companion 318 Nasal CPAP System; May, 1993.
Neilcor Puritan Bennett; Announcing the Goodnight 314 and Goodknight 318 Nasal CPAP Systems.
Puritan Bennett; Clean, Quiet, and Comfortable . . . The Companion's 515 Nasal CPAP Systems; Jun. 1988.
DeVilbiss Night Guard Nasal CPAP for the Treatment of Obstructive Sleep Apnea.
Sunrise; DeVilbiss Horizon LT 8001 Nasal CPAP Therapy Small in Size, big features.
DeVilbiss; Revitalizer Soft Start: The Facts Speak for Themselves.
Tranquility; Performance CPAP Advantage.
Healthdyne International; Tranquility Plus.
Respironics Inc.; Respironics' Solo CPAP System Provides Simiplified OSA Therapy at an Outstanding value; Sep. 19, 1996.
Respironics Inc.; The First Family of OSA Therapy; 1991.
Fisher & Paykai Healthcare; HC200 Series Nasal CPAP Blower & Heated Humidifier.
Pierre Medical; Morphee Plus apparoll de traitment des apnees du sommeil manuel d'utillisation.
Weinmann: Hamburg; Somnotron nCPAP–Great WM 2300.
Puritan Bennett; 513a Part of Our Blueprint for the Future; Mar. 1990.
Puritan Bennett; Companion 320 I/E Bi–Level Respiratory System; Apr. 1993.
ResMed; Sullivan VPAP II & II ST.
ResMed; The Sullivan V Family of CPAP Systems.
ResMed; The AutoSet Portable II.
ResMed; Sullivan Nasal CPAP System.
ResMed; The Sullivan IIID.
ResMed; The Sullivan Comfort.
DeVilbiss a Division of Sunrise Medical; Expand Your Horizons with the Horizons.
Healthdyne Technologies; Home Health Care Dealer; The Journal of Home Medical Equipment and Services/Supplier; Nov. and Dec. 1997.
Airstep: Medical Products . . . . . Stand the Test of Time.
MAP Medical Progress for Physician and Patient; The Gentle Therapy for Sleep–Related Breathing Disorders.
Taema; Ventilation CP 90.
DPAP: Breath, by breath, by breath.
Lifecare: Smallest, Quietest, Smartest.
Lifecare: Quiet CPAP System for Maximum Compliance; 1991.
Lifecare; Software Nasal Mask, Custom Nasal Masks; 1991.
Nidek Medical; Silenzio.
Weinmann: Just to Fell Well, Sensitive Sleep Apnea Therapy with Somnotron 3 and Somno–Mask System.
Respironics Inc.; Aria CPAP System.
Respironics Inc.: Sleep Easy III A New Dawn in Patient Compliance.
Respironics Inc.; Multiple Choice REMstar Choice Nasal CPAP System.
Maxll nCPAP and Moritz II Bi–Level Brochure.
PV 101 Bi–Level CPAP and PV 102 Bi–Level Time; pp. 1–3.
Healthdyne International; Tranquility Quest. The Compact CPAP for Greater patient comfort.

* cited by examiner

MONITORING THE OCCURRENCE OF APNEIC AND HYPOPNEIC AROUSALS

This is a continuation of co-pending application Ser. No. 08/894,093, filed on Dec. 22, 1997, which is hereby incorporated by reference in its entirety.

FIELD OF THE INVENTION

This invention relates to methods and apparatus for the determination or monitoring of arousals that are indicative of an apneic or hypopneic episode. An "A/H episode", as used hereafter, is to be understood as including both obstructive apneas (lack of breathing) or hypopneas (reduction in breathing) occurring during sleep.

BACKGROUND OF THE INVENTION

People suffering from Obstructive Sleep Apnea (OSA) and related conditions experience many A/H episodes during sleep. The conventional treatment for OSA is the well known Continuous Positive Airway Pressure (CPAP) treatment. An A/H episode often has an associated arousal, which is a nervous system response to low blood oxygen level and/or high blood carbon dioxide level.

The condition of OSA normally is diagnosed by laboratory based polysomnography (PSG). PSG involves the measurement of sleep and respiratory variables including EEG, EOG, chin EMG, ECG, respiratory activity, nasal airflow, chest and abdominal movements, abdominal effort and oxygen saturation. The data gathered leads to a calculation of the Respiratory Disturbance Index (RDI) which is the average number of arousals per hour due to respiratory disturbance. PSG is uncomfortable for a patient due to the placement of numerous electrodes on the patient's head or face and the wearing of a mask or nasal prongs. PSG is an expensive procedure and has the inconvenience of requiring the patient to attend a sleep clinic for a whole night requiring continuous technician attendance.

In the clinic, cortical arousals can be detected by measuring and interpreting, either automatically or by eye, changes in the patient's EEG and EMG. Arousals are an important indicator of the amount and quality of sleep obtained by a patient and the degree of severity of the patient's apneas.

To obtain a display of the EEG, electrodes must be attached to the patient's head and the signals from these electrodes passed through high gain amplifiers before subsequent display and recording. This is often inconvenient and time consuming; the signals also can become distorted or disappear due to electrode dislodgement or other artefacts such as sweating. To detect an arousal, the EEG, once displayed, requires interpretation either visually by a skilled operator or automatically by a computer-based analysis system. Apart from the difficulties of attaining accurate EEG data, EEG apparatus also is relatively more expensive than much other biomedical apparatus.

EEG data on its own is not an accurate determination of the occurrence of A/H episodes—an arousal can be due to other factors as noted.

Prior art disclosures that form background information to the present invention include (a) R. Ferber, et al, "ASDA Standards of Practice—Portable Recording in the Assessment of Obstructive Sleep Apnea", Sleep, 17(4): 378–392, 1994; (b) L. FeriniStrambi, et al, "Heart rate variability during sleep in snorers with and without obstructive sleep apnea", Chest, 102(4): 1023–7, Oct. 1992; and (c) C. Guilleminault, et al, "A review of 50 children with obstructive sleep apnea syndrome", Lung, 159:275–287, 1981.

SUMMARY OF THE INVENTION

It is an object of the present invention to overcome or at least ameliorate one or more of the problems with the prior art. In one preferred form the invention seeks to provide a method and apparatus for monitoring the occurrence of arousals due to A/H episodes. The invention in another broad form has as an object the determination of an index of sleep quality that can be used as a diagnostic indicator of a person suffering from conditions such as OSA. Yet further, the invention has as an object the provision of diagnostic apparatus for the recording the occurrence of A/H episodes. A preferred embodiment particularly contemplates detecting sympathetic arousals indicative of A/H episodes by signals derived from a patient which are easier to detect than by EEG, and by use of apparatus that is less costly than that for EEG.

It has been determined that the coincident occurrence of change in the sympathetic physiological variable of sweating and another physiological variable, or of a change in at least two sympathetic physiological variables not necessarily including sweating, is indicative of an arousal associated with an apneic or hypopneic episode.

Therefore, the invention discloses apparatus for monitoring the occurrence of arousals associated with apneic or hypopneic episodes, the apparatus comprising: sensor means for obtaining two or more signals from a patient, one signal representative of skin conductance and the other signals each representative of a physiological variable; and means for correlating said skin conductance signal and at least one other said signal, a coincident change in at least said skin conductance signal and said at least one other said signal being indicative of the occurrence of an arousal.

The correlation can be other than a correlation in the strict mathematical sense, including coincident visual inspection, logical ANDing, indicator voting or weighted sums relative to a threshold.

Preferably, the sensor means comprises electrodes attachable to a patient's body. The signals derived from the electrodes can be signal-conditioned. Furthermore, the means for correlating includes data processing means. Each said signal can have an associated confidence level so that a weighting can be applied in the correlation.

The invention further discloses a method for monitoring the occurrence of arousals associated with apneic or hypopneic episodes, the method comprising the steps of: obtaining two or more signals from a patient, one signal representative of skin conductance and the other signals each representative of a physiological variable; correlating the skin conductance signal and at least one other said signal; and determining whether a coincident change in at least said skin conductance signal and said at least one other signal occurs as an indication of the occurrence of an arousal.

The changes in physiological states can include reduction in blood oxygen saturation, change in heart rate, change in skin conductance, change in skin temperature, increase in blood pressure and changes in breathing sounds.

The invention further discloses apparatus for the diagnosis of apneic or hypopneic episodes resulting in arousals, the apparatus comprising: sensor means for obtaining from a patient two or more signals, each signal representative of a physiological variable and including skin conductance; and means for correlating said two or more signals, one or more coincident changes in at least said skin conductance signal and one other said signal being indicative of an arousal associated with an apneic or hypopneic episode.

The invention yet further discloses a method for the diagnosis of apneic or hypopneic episodes resulting in arousals, the method comprising the steps of: obtaining two or more signals from a patient, each signal representative of a physiological variable and including skin conductance; storing said signals as a time sequence; following completion of obtaining said signals, correlating said two or more signals; and determining whether a coincident change in at least said skin conductance signal and one other said signal occurs as an indication of the occurrence of an arousal associated with an apneic or hypopneic episode.

The invention yet further discloses apparatus for the acquisition of data from a patient from which the diagnosis of apneic or hypopneic episodes resulting in arousals can be made, the apparatus comprising: sensor means for obtaining from the patient two or more signals, each signal representative of a physiological variable and including skin conductance; and a memory for storing said signals in a time sequence for subsequent correlation.

The invention yet further discloses a method for the determination for a patient of an index of sleep quality, the method comprising the steps of: obtaining two or more signals from the patient, each signal representative of a physiological variable; correlating said two or more signals; and recording instances where there is a coincident change in said correlated signals, the number of instances of coincidence being proportional to said index.

The invention yet further discloses apparatus for monitoring the occurrence of sympathetic arousals associated with apneic or hypopneic episodes, the apparatus comprising: sensor means for obtaining two or more signals from a patient, each signal representative of a sympathetic physiological variable; and means for correlating said two or more signals, a coincident change in at least two of said signals being indicative of the occurrence of a said arousal.

The invention yet further discloses a method for monitoring the occurrence of sympathetic arousals associated with apneic or hypopneic episodes, the method comprising the steps of obtaining two or more signals from a patient, each signal representative of a sympathetic physiological variable; and correlating said two or more signals whereby a coincident change in at least two of said signals is indicative of the occurrence of a said arousal.

Embodiments of the invention have the advantage of being non-invasive. This is of particular importance when diagnosis of conditions such as OSA must be undertaken on a baby or small child who may be disturbed by the conventional PSG apparatus.

One embodiment, relating to apparatus for the acquisition of data from which the diagnosis of apneic or hypopneic episodes, and thus the likelihood of the presence of conditions including OSA exist in a patient, can, in the first instance, substitute for a conventional sleep study and allow a candidate to collect data when in the home in a non-invasive manner. The data then can be analysed by a medical practitioner and a determination made of whether further detailed investigations need to be conducted.

DESCRIPTION OF PREFERRED EMBODIMENTS

The sequence of events leading to an arousal due to an apnea or hypopnea are as follows:

1. The patient's upper airway obstructs as they try to inspire, or the central nervous system drive to breathe is inhibited and the patient makes no effort to breathe.
2. The oxygen level in the patient's arterial blood begins to fall and the carbon dioxide level rises.
3. After some time, which may exceed a minute, blood gas sensitive receptors in the carotid and/or aortic arteries force an arousal causing the patient to partially wake and recommence breathing.

This sequence is associated with a number of physiological changes (apart from those of the EEG referred to above) some of which are driven by the sympathetic nervous system which can be monitored:

1. A fall in blood oxygen saturation ($SaO_2$) with subsequent post-apneic rise. $SaO_2$ can be measured by pulse oximetry.
2. A decrease in heart rate as the patient's hypercapnia increases, followed by an increase when they arouse and restart breathing. Heart rate can be measured by ECG techniques.
3. A change in skin conductance due to sweating, measured by application of an electrical potential to measure conductance/impedance.
4. Increase in blood pressure. Blood pressure can be measured by continuous sphygomomanometry.
5. Change in constriction of blood vessels in the skin leading to a change in skin temperature and a change in tissue volume, particularly that in the fingers. This can be measured by plethysmography.
6. A reduction in breathing sounds as the apnea occurs followed by a snore or snort when the apnea is broken.

Taken separately, each of the above changes is only ambiguously related to an arousal after an obstructive event. Each also is subject to artefacts in the signal which are a function of how it is measured. However, by combining several of the above measurements, a much more artefact-free and specific diagnostic indicator of an arousal due to an A/H episode can be obtained.

Figure 1:
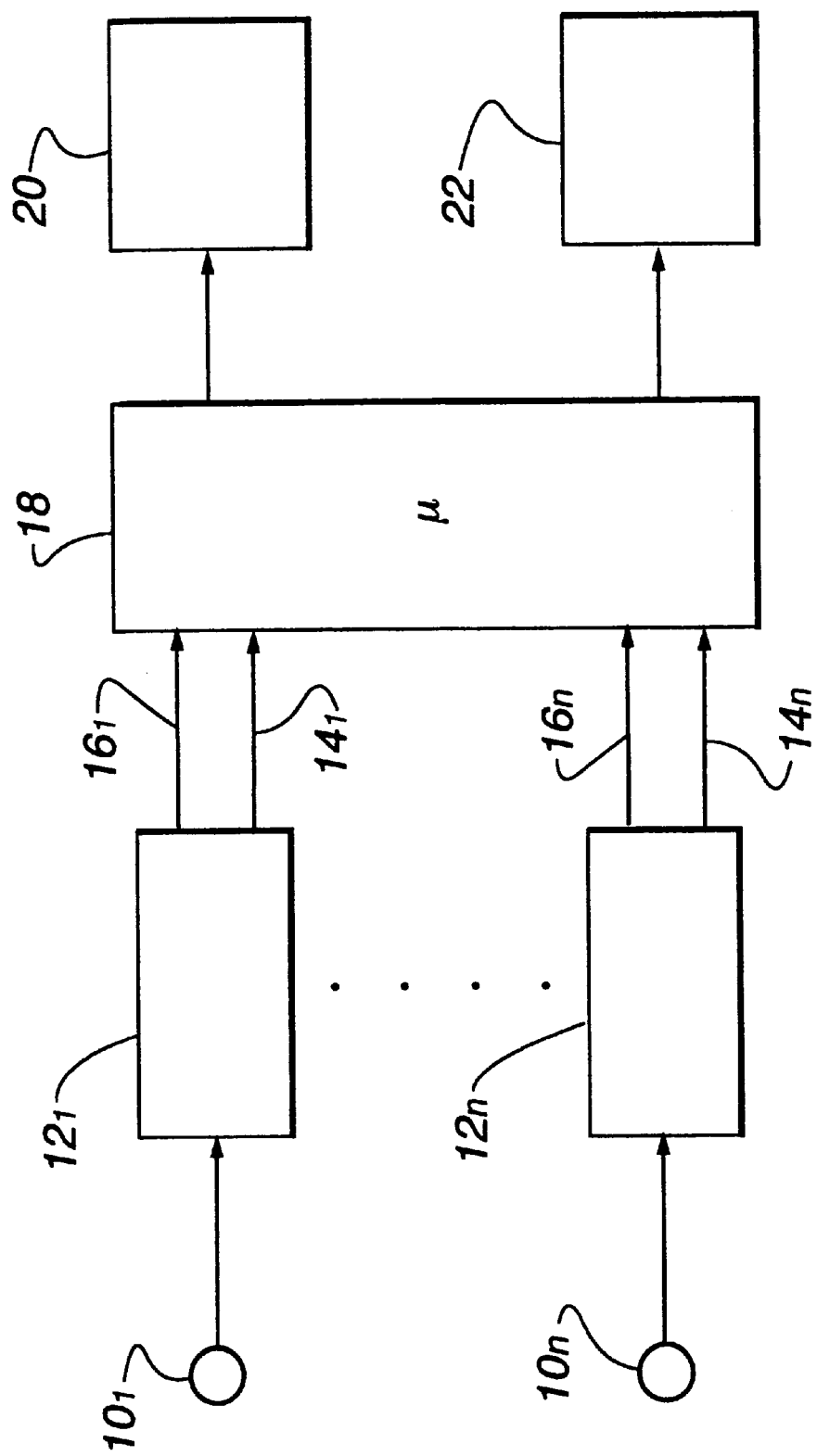
FIG. 1 is a schematic block diagram of diagnostic apparatus embodying the invention.

FIG. 1 shows a plurality of sensors $10_1$–$10_n$ from which signals of the type described above are obtained from the patient. The sensors typically will comprise a sensing portion to detect physiological functions such as blood oxygen saturation, heart rate, skin conductance, blood pressure, skin temperature and audible noises, coupled with amplifying/buffering devices to derive an electrical signal.

The electrical signals each are passed to a corresponding preprocessing section $12_1$–$12_n$. The conditioning typically can include averaging, thresholding linearisation and differentiation for those signals which exhibit a marked change. Each of the n signals has a characteristic pattern or range of patterns associated with apneic and hypopneic events. Each matching pattern serves as an indicator for an apneic or hypopneic event. A characteristic pattern for each signal is as follows.

1. The blood oxygen saturation signal ($SaO_2$) is low-pass filtered, resulting in a baseline value. Signal values which differ from the baseline by a predetermined threshold, typically 3%, are positive indicators.

2. The heart rate signal is low-pass filtered to remove high frequency components, including the sinus rhythm. This signal is then differentiated, so that changes in the heart rate are evident. A fall in the heart rate followed by a marked increase in heart rate is an indicator. When the difference between the slowest and fastest heart-rate is greater than a specified minimum, typically 20 beats per minute, the indicator scores positively.

3. The skin conductance is low-pass filtered, resulting in a baseline value, then is high-pass filtered to accentuate changes. When the conductance increases above a specific ratio of the baseline, typically 100%, the indicator scores positively.

4. The blood pressure signal (both systolic and diastolic) is low-pass filtered to produce a baseline value. The elevation of the blood pressure by more than a predetermined threshold, typically 25%, results in a positive indicator.

5. The skin temperature is low-pass filtered to produce a baseline value. If the skin temperature falls below a specific threshold from the baseline, typically between 0.5 and 1.0° C., the indicator is positive.

6. Breathing sounds are band-pass filtered, typically between 30 and 300 Hz. The energy from this signal is estimated by squaring or rectifying the filtered signal, and is used as a measure of snore intensity. A significant fall in the snore intensity, typically by 6 dB, followed by a sharp increase, is a positive indicator.

The conditioned signals $14_1$–$14_n$, together with a quality signal $16_1$–$16_n$ giving a measure of the quality (confidence) of the signal, are passed to a multi-input processing device 18. The multiple input signals are processed algorithmically, with ones of the signals 14 having the higher quality factor being given more weight.

The detection of an isolated matching pattern does not signify an apneic or hypopneic event. However, the coincidence of two or more of these indicators increases the confidence of event detection. Various algorithms can be used:

1. Indicator ANDing, whereby each of the indicators must be positive to indicate an arousal.
2. Indicator voting, whereby most of the indicators must be positive to indicate an arousal.
3. Weighted sum, whereby each of the indicators has a predetermined weight. The products of each indicator and its weight are accumulated. The sum indicates an arousal if the sum is above a predetermined threshold.

The processing device 18 thus makes a determination of whether an arousal associated with an A/H episode has occurred, and further determines the percentage chance that this 'diagnosis' is correct, and yet further provides a determination of the duration of the A/H episode that preceded the arousal. These determined functions are logged to a memory device 20 for subsequent analysis, for example by plotting with time and observing coincidences, and also can be indicated on a display device 22 in real time.

From this information an index of arousals can be compiled, typically as arousals per hour, providing an alternative indicator to ROI, as previously discussed, to serve as a useful indicator of sleep quality.

In another embodiment the signals obtained from the sensors can be directly stored in the memory device 20 in a time sequence for subsequent correlative processing by the processing device 18, or by a processor independent of the data acquisition module. This embodiment can serve as a data acquisition device for home usage, with the correlative processing occurring at a medical practitioner's surgery (for example) at a later time.

Particular embodiments now will be described, relating to clinical measurements performed on three patients, and for which the physiological variables measured include skin conductance and heart rate particularly cardiac rate, both of which are sympathetic variables).

Heart rate is measured by a conventional technique, namely three lead ECG. It is preferred that the electrodes are located at the patient's body's extremities to avoid apprehension and reduce the likelihood of unwanted artifacts due to gross body movement.

The skin conductance measurement similarly is performed at the body's extremities, in one case being on the sole of a foot where sweat glands are concentrated. An alternate site is the forehead. Skin conductance is to be understood as the reciprocal of skin resistance, which is affected by sweating. In the complex number domain, conductance is the real part of skin admittance. As follows, skin also exhibits a reactive property (essentially a capacitance), the reciprocal of which is the susceptance.

Figure 2:
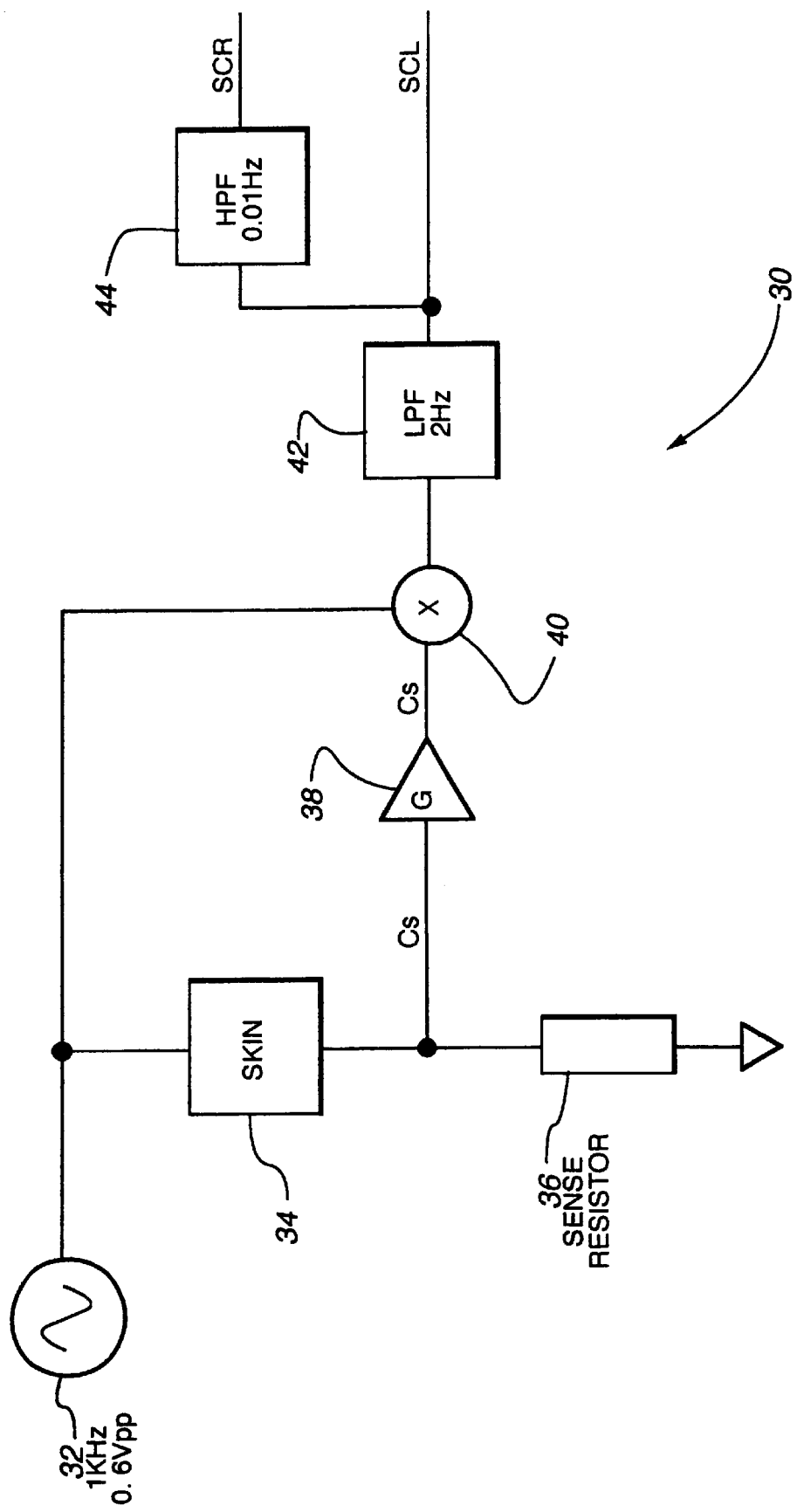
FIG. 2 is a schematic block diagram of a circuit for measuring skin conductance.

FIG. 2 shows a schematic block diagram of a skin conductance measurement system 30 representing one form of a sensor 10 and preprocessing section 12. An oscillator 32 applies a 1 kHz signal of approximately 0.6 V signal between two electrodes placed apart on the sole of the patient's foot, thereby applying an excitation to the patient's skin 34. The current passing through the electrodes is dependent upon the conductance and susceptance of the skin and interconnecting tissue.

A sense resistor 36 converts the current to a signal voltage $c_S$, which is amplified by an amplifier 38. A demodulator circuit 40,42 removes the effects of the skin susceptance (i.e. due to the skin's capacitance) from the amplified signal $C_S$, so that the resulting signal, SCL, is proportional to the skin conductance (level). The baseline of the SCL is removed by a high pass filter 44 and amplified (not shown) so that responses to arousals are accentuated and more easily monitored. The resultant signal, SCR, is indicative of the skin conductance response.

Figure 3:
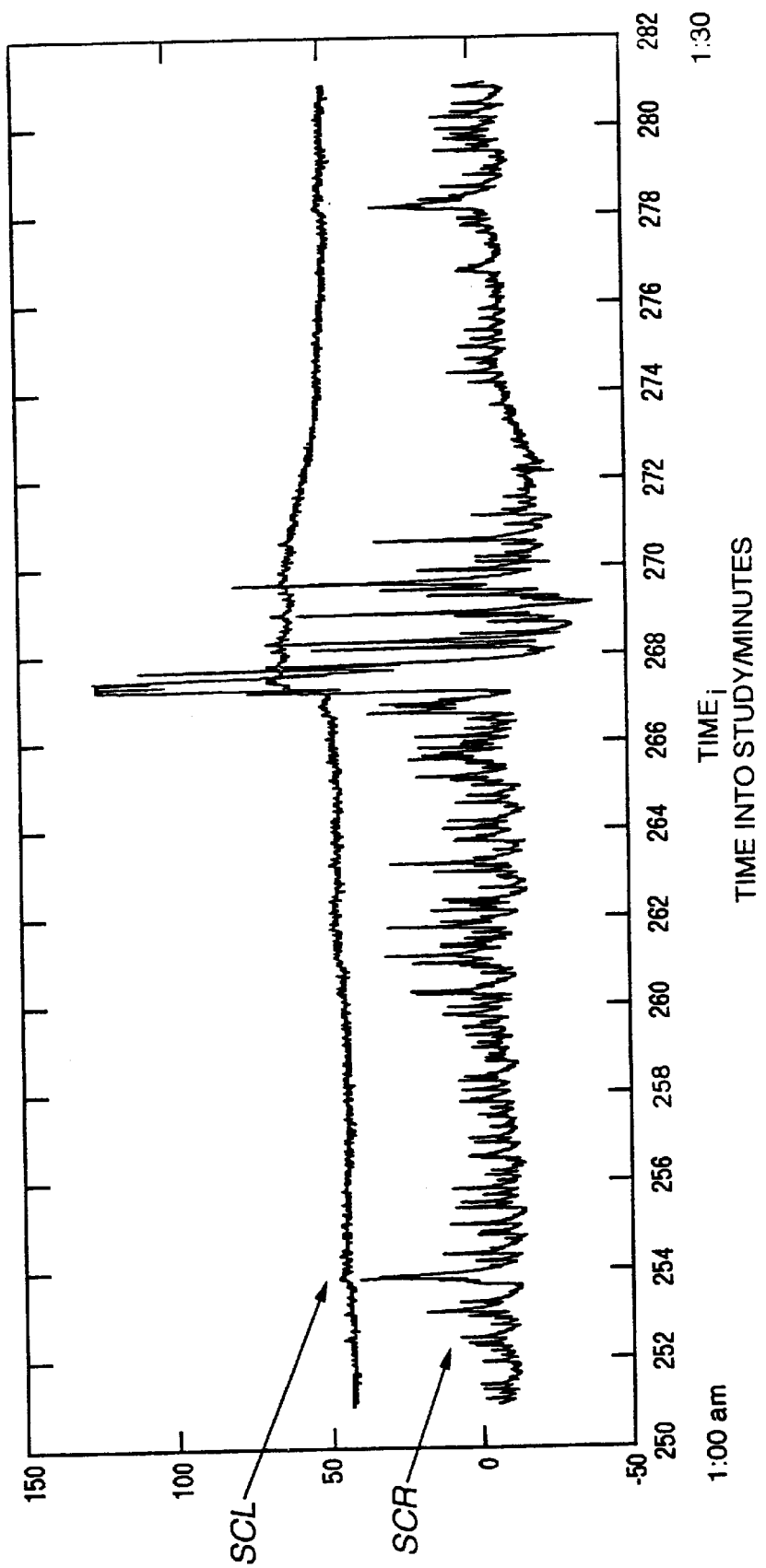
FIG. 3 is a plot of skin conductance with time.

FIG. 3 shows a time window of one half an hour during a sleep study performed on a patient known to be a sufferer of Obstructive Sleep Apnea. The upper trace represents the skin conductance SCL, and the lower trace the skin conductance response SCR. The sensed response at approximately t=267.5 minutes corresponded with an apneic arousal otherwise determined by PSG. Skin conductance thus is a reliable partial indicator of an arousal associated with an A/H episode.

Figure 4:
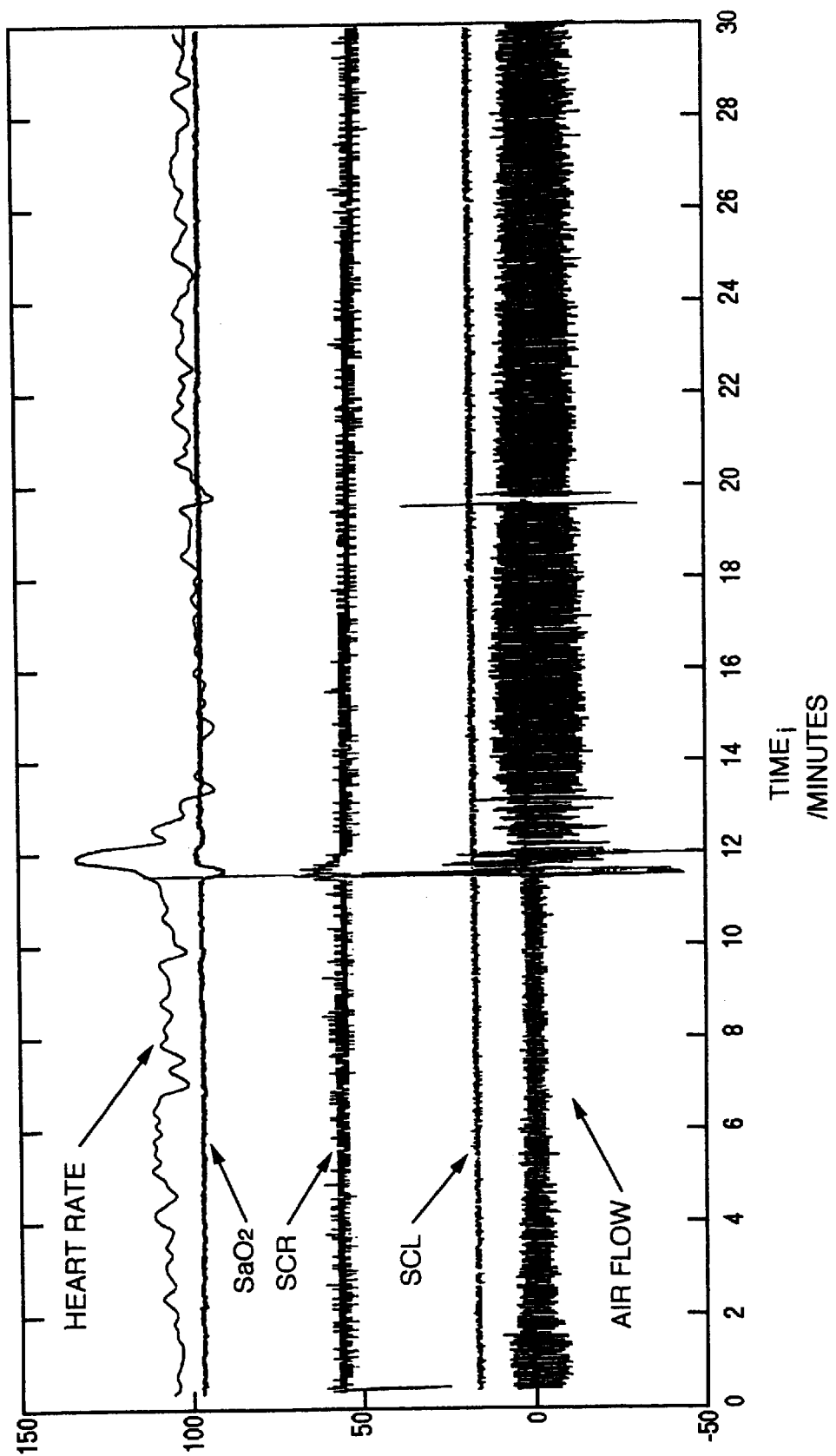
FIG. 4 is a plot of skin conductance together with airflow rate, heart rate and $SaO_2$.

FIG. 4 shows an excerpt from a sleep study conducted on a different patient showing a relevant 30 minute window. The patient is a known sufferer of OSA. The uppermost trace is heart rate filtered over one minute to remove sinus rhythm. The units are beats per minute, and the measurement is made with a pulse oximeter. The second trace (in descending order) is blood oxygen saturation ($SaO_2$) also measured with a pulse oximeter. The scale is 0–100%. The third trace is the SCR phase reference signal and the fourth trace the SCL base reference signal as measures of skin conductance. The units of conductance are relative only. The lowermost trace is of respiratory airflow measured with nasal cannulae and a pressure transducer.

FIG. 4 shows a continuous decrease in nasal airflow until approximately t=11 minutes corresponding to a hypopneic event. At this point nasal airflow increased with the taking of a sudden deep breath. The $SaO_2$ trace shows a corresponding fall of approximately 5%, which, because of heavy filtering, appears after the resumption of normal breathing, although in fact was coincident with the sudden deep breath. The chain of events was shallow breathing (hyponea), followed by a fall in $SaO_2$, followed by a resumption of normal breathing. Associated with the arousal causing the resumption of normal breathing is tachycardia, with the heart rate increasing by about 20 bpm. The arousal is coincident in time with the sudden increase in skin conductance and heart rate. Thus these two quantities can be utilised in concert as an indicator of arousals associated with A/H episodes.

Interestingly, at approximately t=20 minutes, there is a sudden interruption in respiratory airflow as a result of the patient sighing, however there is no corresponding indicator in either skin conductance or heart rate to suggest that the cessation of flow was due to an apnea.

The data indicates that the correlation of skin conductance with one or more other physiological variables (whether associated with the sympathetic nervous system or not) or any two or more sympathetic physiological variables (for example blood pressure and heart rate), is an accurate determinant of the occurrence of an arousal associated with an A/H episode. Further, it is believed that the correlation of two sympathetic physiological variables, not necessarily including skin conductance, and for example heart rate and blood pressure, also is an accurate determinant.

Figure 5:
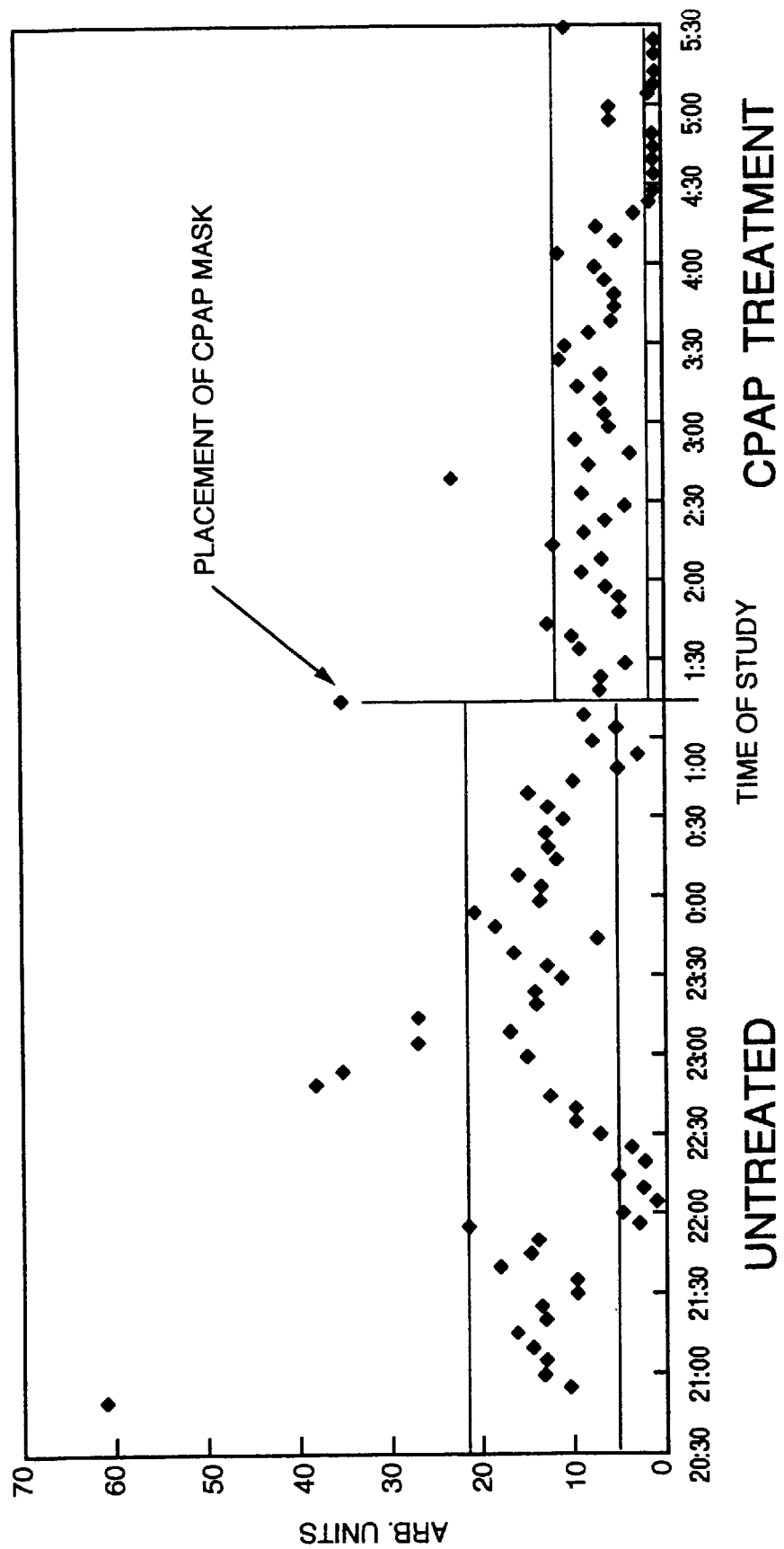
FIG. 5 is a plot of skin conductance measured periodically both before and during CPAP treatment is implemented.

FIG. 5 shows a plot of the variance of skin conductance for the third patient during a sleep study in which between t=20:30 hours and t=1:15 hours no CPAP treatment was in place, and between t=1:15 hours and t=5:30 hours CPAP treatment was in place. The sampling points are at five minute epochs. The 10 and 90 centiles have been shown. The plot indicates the reduction in variance of skin conductance both before and after the commencement of CPAP treatment as an indication of the reduction in the number of arousals due to A/H episodes and thus the reliability of skin conductance as a partial indicator of A/H episodes.

In summary, embodiments of the invention can serve to monitor the occurrence of apneic or hypopneic episodes, to diagnose the occurrence of A/H episodes resulting in arousals, to acquire data from which the diagnosis of A/H episodes resulting from arousals can be made, to determine an index of sleep quality, and to monitor the sympathetic nervous system.

What is claimed is:

1. A method for the determination for a patient of an index of sleep quality, the method comprising the steps of:
    obtaining two or more signals from the patient, each signal representative of a physiological variable;
    correlating said two or more signals; and
    recording instances where there is a coincident change in said correlated signals, the number of instances of coincidence being proportional to said index, and the number of instances of coincidence being scaled linearly to give said index.

2. A method as claimed in claim 1, comprising the further step of storing said signals as a time sequence, and performing said correlation only upon completion of said signal obtaining step.

3. A method as claimed in claim 1, wherein said physiological variables are associated only with the sympathetic nervous system.

4. Apparatus for monitoring the occurrence of sympathetic arousals associated with apneic or hypopneic episodes, the apparatus comprising:
    sensor means for obtaining two or more signals from a patient, each signal representative of a sympathetic physiological variable;
    means for correlating said two or more signals, a coincident change in at least two of said signals being indicative of the occurrence of an arousal; and
    means for recording the occurrence of arousals.

5. A method for monitoring the occurrence of sympathetic arousals associated with apneic or hypopneic episodes, the method comprising the steps of:
    obtaining two or more signals from a patient, each signal representative of a sympathetic physiological variable;
    correlating said two or more signals whereby a coincident change in at least two of said signals is indicative of the occurrence of a said arousal; and
    recording the occurrence of arousals.

6. Apparatus for determining occurrence of at least one of apneic and hypopneic arousals in a patient, comprising:
    a skin conductance sensor connectable to an extremity of the patient;
    apparatus, associated with the skin conductance sensor, that processes output of the skin conductance sensor to determine whether the skin conductance sensor output indicates at least one of an apneic and an hypopneic arousal;
    a heart rate sensor connectable to an extremity of the patient;
    apparatus, associated with the heart rate sensor, that processes output of the heart rate sensor to determine whether the heart rate sensor output indicates at least one of an apneic and a hypopneic arousal; and
    apparatus that determines whether a positive indicator in skin conductance coincides with a positive indicator in heart rate.

7. Apparatus as claimed in claim 6, wherein the extremity to which the skin conductance sensor is connectable is the sole of the patient's foot.

8. Apparatus as claimed in claim 6, wherein the extremity to which the skin conductance sensor is connectable is the patient's forehead.

9. Apparatus as claimed in claim 6, wherein the heart rate is measured using a three lead ECG.

10. Apparatus as claimed in claim 6, wherein the heart rate is measured using a pulse oximeter.

11. A method of determining occurrence of at least one of apneic and hypopneic arousals in a patient in an overnight study, comprising:
    monitoring variation in a patient's skin conductance and at least one other physiological variable indicative of sympathetic nervous system activity;
    providing no CPAP treatment during a first portion of the overnight study;
    providing CPAP treatment during a second portion of the overnight study; and
    determining that at least one of an apneic and a hypopneic arousal has occurred when a positive indicator in skin conductance coincides with a positive indicator in said at least one other physiological variable.

12. A method as claimed in claim 11, wherein the first portion of the overnight study occurs from approximately 20:30 hours to 1:15 hours.

13. A method as claimed in claim 11, wherein the second portion of the overnight study occurs from approximately 1:15 hours to 5:30 hours.

14. A method as claimed in claim 11, further including determining an index of sleep quality from a number of apneic and hypopneic arousals that have been determined during the overnight study.

* * * * *